United States Patent
Babayoff et al.

(12) 
(10) Patent No.: US 9,937,021 B2
(45) Date of Patent: *Apr. 10, 2018

(54) DENTAL IMAGING INSTRUMENT HAVING AN AIR STREAM AUXILIARY

(71) Applicant: ALIGN TECHNOLOGY, INC., San Jose, CA (US)

(72) Inventors: Noam Babayoff, Rishon le Zion (IL); Eldad Taub, Reut (IL); Avi Kopelman, Tenalfy, NJ (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,366

(22) Filed: May 18, 2016

(65) Prior Publication Data

US 2016/0256244 A1 Sep. 8, 2016

Related U.S. Application Data

(63) Continuation of application No. 13/082,630, filed on Apr. 8, 2011, now abandoned, which is a continuation
(Continued)

(51) Int. Cl.
*A61C 3/00* (2006.01)
*A61C 9/00* (2006.01)
(Continued)

(52) U.S. Cl.
CPC .............. *A61C 9/006* (2013.01); *A61B 1/253* (2013.01); *A61C 17/022* (2013.01); *A61C 17/0208* (2013.01)

(58) Field of Classification Search
CPC ....... A61B 1/24; A61B 5/0064; A61B 5/0088; A61B 5/4547; A61B 2560/0456;
(Continued)

(56) References Cited

U.S. PATENT DOCUMENTS 2,467,432 A   4/1949  Kesling
3,407,500 A   10/1968 Kesling
(Continued)

FOREIGN PATENT DOCUMENTS

AU     3031677 A    5/1979
AU     517102 B2    7/1981
(Continued)

OTHER PUBLICATIONS

AADR. American Association for Dental Research, Summary of Activities, Mar. 20-23, 1980, Los ngeles, CA, p. 195.
(Continued)

*Primary Examiner* — Heidi M Eide
(74) *Attorney, Agent, or Firm* — Wilson Sonsini Goodrich & Rosati (57) ABSTRACT

A dental instrument and method for imaging the three-dimensional topography of one or more teeth in the oral cavity of an individual is provided. The instrument includes a probe insertable into the oral cavity to receive the image of these surfaces which can then be processed. Combined with the probe is an auxiliary which projects an air stream toward the surface to be imaged by the probe and acts to evaporate and remove from these surfaces a liquid film coating formed by saliva and other fluids present in the oral cavity, to render these surfaces dry and to enhance their reflectivity and in doing so, provide clearer images.

16 Claims, 2 Drawing Sheets

Related U.S. Application Data of application No. 11/703,085, filed on Feb. 7, 2007, now Pat. No. 7,946,846, which is a continuation of application No. 10/174,271, filed on Jun. 18, 2002, now Pat. No. 7,255,558.

(51) Int. Cl.
  *A61B 1/253* (2006.01)
  *A61C 17/02* (2006.01)
  *A61C 17/022* (2006.01)

(58) Field of Classification Search
  CPC ..... A61B 1/253; A61C 9/006; A61C 17/0208; A61C 17/022
  See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,184,175 A | 1/1980 | Mullane, Jr. |
| 4,195,046 A | 3/1980 | Kesling |
| 4,201,200 A | 5/1980 | Hubner |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,725,232 A * | 2/1988 | Hatakeyama ........ A61C 1/0038 433/126 |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,149 A | 8/1990 | Duret et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,115,307 A | 5/1992 | Cooper et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,178,536 A | 1/1993 | Werly et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,350,299 A | 9/1994 | Gallant |
| 5,368,478 A | 11/1994 | Andreiko et al. |
| 5,381,236 A | 1/1995 | Morgan |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| 5,484,283 A * | 1/1996 | Franetzki ........ A61B 1/042 433/116 |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,737,084 A | 4/1998 | Ishihara |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,951,284 A | 9/1999 | Lake |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |

(56) References Cited

U.S. PATENT DOCUMENTS

| | | | |
|---|---|---|---|
| 6,015,289 | A | 1/2000 | Andreiko et al. |
| 6,044,309 | A | 3/2000 | Honda |
| 6,049,743 | A | 4/2000 | Baba |
| 6,062,861 | A | 5/2000 | Andersson |
| 6,068,482 | A | 5/2000 | Snow |
| 6,099,314 | A | 8/2000 | Kopelman et al. |
| 6,123,544 | A | 9/2000 | Cleary |
| 6,152,731 | A | 11/2000 | Jordon et al. |
| 6,183,248 | B1 | 2/2001 | Chishti et al. |
| 6,190,165 | B1 | 2/2001 | Andreiko et al. |
| 6,217,325 | B1 | 4/2001 | Chishti et al. |
| 6,217,334 | B1 | 4/2001 | Hultgren |
| 6,244,861 | B1 | 6/2001 | Andreiko et al. |
| 6,254,597 | B1 | 7/2001 | Rizoiu et al. |
| 6,263,234 | B1 | 7/2001 | Engelhardt et al. |
| 6,309,215 | B1 | 10/2001 | Phan et al. |
| 6,315,553 | B1 | 11/2001 | Sachdeva et al. |
| 6,322,359 | B1 | 11/2001 | Jordan et al. |
| 6,350,120 | B1 | 2/2002 | Sachdeva et al. |
| 6,359,680 | B1 | 3/2002 | Rubbed |
| 6,382,975 | B1 | 5/2002 | Poirier |
| 6,386,867 | B1 * | 5/2002 | Durbin .................... A61C 9/00 433/214 |
| 6,398,548 | B1 | 6/2002 | Muhammad et al. |
| 6,402,707 | B1 | 6/2002 | Ernst |
| 6,443,729 | B1 | 9/2002 | Watson |
| 6,468,076 | B2 | 10/2002 | Kawamura |
| 6,482,298 | B1 | 11/2002 | Bhatnagar |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,629,840 | B2 | 10/2003 | Chishti et al. |
| 6,697,164 | B1 | 2/2004 | Babayoff et al. |
| 6,705,863 | B2 | 3/2004 | Phan et al. |
| 6,722,880 | B2 | 4/2004 | Chishti et al. |
| 6,885,464 | B1 | 4/2005 | Pfeiffer et al. |
| 7,255,558 | B2 | 8/2007 | Babayoff et al. |
| 7,946,846 | B2 | 5/2011 | Babayoff et al. |
| 2001/0012605 | A1 * | 8/2001 | Kawamura ............... A61B 1/24 433/29 |
| 2002/0006597 | A1 | 1/2002 | Andreiko et al. |
| 2002/0015934 | A1 | 2/2002 | Rubbert et al. |
| 2002/0055082 | A1 | 5/2002 | Durbin et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2003/0232302 | A1 | 12/2003 | Babayoff et al. |
| 2004/0128010 | A1 | 7/2004 | Pavlovskaia et al. |
| 2005/0055118 | A1 | 3/2005 | Nikolskiy et al. |
| 2007/0134617 | A1 | 6/2007 | Babayoff et al. |
| 2011/0183283 | A1 | 7/2011 | Babayoff et al. |

FOREIGN PATENT DOCUMENTS

| | | | |
|---|---|---|---|
| AU | 5598894 A | | 6/1994 |
| CA | 1121955 | | 4/1982 |
| DE | 2749802 | | 5/1978 |
| DE | 69327661 T | | 7/2000 |
| EP | 0091876 A1 | | 10/1983 |
| EP | 0299490 A2 | | 1/1989 |
| EP | 0376873 A2 | | 7/1990 |
| EP | 0490848 A2 | | 6/1992 |
| EP | 0541500 A1 | | 5/1993 |
| EP | 0667753 B1 | | 8/1995 |
| EP | 0731673 B1 | | 9/1996 |
| EP | 0774933 B1 | | 5/1997 |
| ES | 463897 | | 1/1980 |
| FR | 2369828 A1 | | 6/1978 |
| FR | 2652256 A1 | | 3/1991 |
| GB | 15500777 | | 8/1979 |
| JP | 53-058191 | | 5/1978 |
| JP | 04-028359 | | 1/1992 |
| JP | 08-508174 | | 9/1996 |
| WO | WO 90/08512 A1 | | 8/1990 |
| WO | WO 91/04713 A1 | | 4/1991 |
| WO | WO 94/10935 A1 | | 5/1994 |
| WO | WO 98/32394 A1 | | 7/1998 |
| WO | WO 98/44865 A1 | | 10/1998 |
| WO | WO 98/58596 A1 | | 12/1998 |
| WO | WO 00/08415 * | 2/2000 | ............ G01B 11/24 |
| WO | WO 00/08415 A1 | | 2/2000 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24.

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. In Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Operation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

(56) References Cited

OTHER PUBLICATIONS

Bourke, "Coordinate System Transformation," (Jun. 1996), p. 1, retrieved from the Internet Nov. 5, 2004, URL <http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone (interview), "Dr. Charles J. Burstone on The Uses of the Computer in Orthodontic Practice (Part 1)," J. Clin. Orthod., 13(7):442-453 (Jul. 1979).

Burstone (interview), "Dr. Charles J. Burstone on The Uses of the Computer in Orthodontic Practice (Part 2)," J. Clin. Orthod., 13(8):539-551 (Aug. 1979).

Burstone et al., Precision Adjustment of the Transpalatal Lingual Arch: Computer Arch Form Predetermination, Am, Journal of Orthodontics, vol. 79, No. 2 (Feb. 1981), pp. 115-133.

Cardinal Industrial Finishes, Powder Coatings information posted at <http://www.cardinalpaint.com> on Aug. 25, 2000, 2 pages.

Carnaghan, "An Alternative to Holograms for the Portrayal of Human Teeth," 4th Int'l. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1: CAD/CAM: The Computer Moves Chairside," "Part 2: F. Duret—A Man With A Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin. Orthod., 7(4):258-265 (Dec. 2001).

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production, pp. 1-7 (Jan. 1992).

Definition for gingiva. Dictionary.com p. 1-3. Retrieved from the internet Nov. 5, 2004 <http://reference.com/search/search?q=gingiva>.

Defranco et al., "Three-Dimensional Large Displacement Analysis of Orthodontic Appliances," J. Biomechanics, 9:793-801 (1976).

Dental Institute University of Zurich Switzerland, Program for International Symposium on Computer Restorations: State of the Art of the CEREC-Method, May 1991, 2 pages total.

Dentrac Corporation, Dentrac document, pp. 4-13 (1992).

Dent-X posted on Sep. 24, 1998 at <http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances-Pro Lab, 1 page (1997).

Duret et al, "CAD-CAM in Dentistry," J. Am. Dent. Assoc. 117:715-720 (Nov. 1988).

Duret et al., "CAD/CAM Imaging in Dentistry," Curr. Opin. Dent., 1:150-154 (1991).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).

Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-228 (Apr. 1989).

Heaven et al. "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa...>.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), lnformatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances—Pro Lab, 1 page 1998).

JCO Interviews, Craig Andreiko, DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

(56) References Cited

OTHER PUBLICATIONS

Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984).
Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "Cerec CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).
Procera Research Projects, "Procera Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp! Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manual utiiisateur, Version 2.0X (in French), 2003, 114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blu . . . The Simple, Affordable, No-Braces Treatment, Allesee Orthodontic Appliances—Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances-Pro Lab

(56) References Cited

OTHER PUBLICATIONS product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports", Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

\* cited by examiner

DENTAL IMAGING INSTRUMENT HAVING AN AIR STREAM AUXILIARY

CROSS-REFERENCE

This application is a continuation of U.S. patent application Ser. No. 13/082,630, filed Apr. 8, 2011, now abandoned, which is a continuation of U.S. patent application Ser. No. 11/703,085, filed Feb. 7, 2007, now U.S. Pat. No. 7,946,846, issued May 24, 2011, which is a continuation of U.S. patent application Ser. No. 10/174,271, filed Jun. 18, 2002, now U.S. Pat. No. 7,255,558, issued Aug. 14, 2007, the entire contents of each of which is incorporated herein by reference.

FIELD OF THE INVENTION

This invention relates generally to dental instruments for imaging the three-dimensional topography of teeth in a patient's oral cavity by means of a probe which projects a beam of light toward the surfaces of the teeth and receives reflections therefrom which are processed to derive the required data.

BACKGROUND OF THE INVENTION

It is a standard procedure in dental practice, when necessary to replace defective teeth in the oral cavity of a patient, to first make a cast impression of these teeth. A technician can from these impressions determine the three-dimensional parameters of a denture to replace the teeth.

It is known in order to avoid the need to make cast impressions to directly measure the teeth optically to obtain data for the computer-assisted design (CAD) or computer-assisted manufacture (CAM) of the replacement. In a typical instrument for this purpose, there is provided an optical probe projecting a light beam towards the surfaces of the teeth to be imaged.

The concern of the present invention is with those imaging instruments for direct optical measurement of a set of teeth which includes a probe to be inserted in the oral cavity to project a light beam toward the surfaces of the teeth and to receive light reflected therefrom which is then processed to obtain the digital data for determining the three-dimensional topology of the teeth.

One such instrument for obtaining the three-dimensional parameters of teeth in order to replace the teeth being imaged is disclosed in U.S. Pat. No. 4,575,805. In the patent, the probe takes the form of a scan head which projects a scanning light beam toward the teeth surfaces.

Also disclosing an imaging instrument for the three-dimensional survey of teeth, to obtain digital constructional data for the computer-controlled manufacture of a tooth replacement is U.S. Pat. No. 5,381,236. Another such instrument is an intra oral scanner disclosed in U.S. Pat. No. 6,359,680.

Of particular prior art interest is the imaging instrument disclosed in the PCT publication WO 00/08415 published 17 Feb. 2000 entitled "Imaging A Three-Dimensional Structure by Confocal Focusing an Array of Light Beams". This instrument is provided with a probe in the form of an endoscope which projects light beams toward the surfaces of the teeth to be imaged and receives light reflected therefrom which is processed to obtain the required digital data.

The problem of viewability encountered when using a dental imaging instrument whose probe projects a light beam to illuminate the surfaces of the teeth to be imaged is comparable to that experienced by eyes viewing these surfaces. If the eyes are heavily coated with a tear film, the resultant image will be blurred, In the case of surfaces of teeth in an oral cavity containing mucous, saliva, and, in some instances, blood resulting from a dental procedure, the surfaces of the teeth are usually then coated with a liquid film composed of these constituents. This liquid film which impairs the ability of an imaging instrument to clearly view the teeth surfaces, cannot easily be dislodged, for the film is ionically attracted to the teeth surfaces and has a surface tension to protect the integrity of the film and resists its evaporation.

Under ideal circumstances, the surfaces of the teeth to be imaged should be free of liquid and perfectly clean and dry to obtain an optimal degree of reflectivity and image clarity. But this can only happen when the surface reflectivity exhibits a Lambert unit of luminescence. A Lambert unit is defined as the brightness of a perfect diffusing surface that radiates or reflects one lumen per square centimeter.

A saliva-mucous liquid film coating the teeth surfaces to be illuminated, does not act as a perfect diffusing surface and therefore does not exhibit optimal reflectivity. And because this film adheres ionically to the tooth surfaces, it cannot just be washed away.

In common use by dentists is an air suction pipe (negative pressure) to suck out from the oral cavity saliva and mucous which interfere with the dental procedure then in progress. Also in common use is a pressured air pipe (positive pressure) which serves to blow away debris from the region in the oral cavity is working. These pipes must be manipulated by the dentist or his assistant so that the air stream (negative or positive) can be directed to the region of interest.

SUMMARY OF THE INVENTION

In the present invention, an auxiliary producing a positive or negative (suction) air stream is combined with a probe of an imaging instrument which is manipulated in the oral cavity to direct a light beam toward teeth surfaces to be illuminated, the auxiliary then also projecting the air stream in the same direction.

An auxiliary in accordance with the invention is combinable with the light-beam projecting probe of any existing dental imaging instrument adapted to survey the three-dimensional topography of teeth in the oral cavity.

It is thus the main object of this invention to provide a dental image acquisition and method for acquiring an image of the three-dimensional topography of a teeth segment in the oral cavity of a subject by means of a probe projecting a beam of light toward these surfaces, the probe being combined with an auxiliary which causes a stream of gas, typically air, to flow over the surfaces to be illuminated to dry these liquid-film coated surfaces to enhance their reflectivity to give rise to a clearer image of the teeth.

While the invention will be described, by way of example, in conjunction with a dental imaging instrument of the type disclosed in the above-identified PCT publication WO 00/08415, it is to be understood that it is applicable to any existing form of imaging instrument having a probe which projects a light beam to illuminate the surfaces of the teeth to be imaged.

Among the significant features of the invention, by which a dental imaging instrument is combined with an air stream auxiliary are the following:

A. The auxiliary can project the air stream towards the liquid film coating the surfaces of the teeth to be imaged at a velocity that disrupts the ionic bond between the liquid film and the teeth surfaces.

B. The auxiliary air stream may be made to be in a pulsatory wave form to produce periodic bursts of air which effectively hammer away at the liquid film to dislodge it from the dental surfaces.

C. The air stream may be heated to a temperature level which promotes rapid evaporation of the liquid film coating the teeth surface, which level can be tolerated by the patient.

D. The heated air stream may act to fully dry the teeth surfaces to enhance their reflectivity and in doing so produce clearer images of the teeth.

E. The auxiliary from which the air stream is projected may be integrated with the probe from which a light beam is projected to illuminate the surfaces of the teeth to be imaged, whereby the air stream is focused on the surfaces to provide rapid drying thereof.

The invention thus provides, by one of its aspects, a dental instrument for imaging the three-dimensional surface topography of a teeth segment consisting of one or more adjacent teeth in the oral cavity of an individual, e.g. in order to acquire digital data regarding the parameters of a replacement or prosthesis for a missing or broken tooth. The instrument includes a probe insertable into the oral cavity to capture an image of the teeth segment. The probe typically also projects a light beam toward the surfaces of the teeth to be imaged. Alternatively, the illumination may also be an independent light source. The captured image is then conveyed to a processor to obtain the required data. Combined with the probe is an auxiliary which by one embodiment projects an air stream toward the surfaces to be imaged by the probe. The air stream acts to evaporate and remove from these surfaces a liquid film coating formed by saliva and other fluids present in the oral cavity. The surfaces thereby become dry and this enhances their reflectivity, to yield clearer images. By another embodiment, the auxiliary includes a suction arrangement that induces an air stream in an opposite direction that may yield a result comparable to that achieved with the embodiment discussed above. In this matter the film coating is sucked away from the teeth.

By another aspect, there is provided a method for imaging the three-dimensional surface topography of a teeth segment. It comprises bringing a probe into proximity of the teeth to be imaged and acquiring the image. The method is characterized in that while acquiring the teeth image causing a stream of gas to flow over the surface of the teeth to be imaged.

In accordance with one embodiment of the invention, said auxiliary induces two air streams, one flowing over the surface of the teeth segment to be imaged, while the other flows over the external optical sensing surface, namely, the external surface of the optical system that acquires the image. In some imaging techniques, e.g. one that makes use of the optical sensing surface such as that disclosed in PCT Publication WO/00/08415, the probe needs to be inserted into the oral cavity and brought into proximity with the teeth to be imaged. In this case, the optical sensing surface may also become coated with a liquid film formed from aerosol particles that exist in the oral cavity or liquid vapor that condenses on the sensing surface.

An optical probe making use of confocal optics is a preferred embodiment in accordance with the invention.

BRIEF DESCRIPTION OF THE DRAWINGS

For a better understanding of the invention as well as other objects and features thereof, reference is made to the annexed drawings in which.

DETAILED DESCRIPTION OF THE INVENTION

As explained above, a dental imaging instrument of the type disclosed in PCT Publication No. WO 00/08415 or others in which a probe directs a beam of light toward the surfaces of the teeth to be imaged and picks up light reflected from these surfaces, is unable to obtain clear images because the liquid film which coats these surfaces degrade their reflectivity.

A liquid film composed mainly of saliva and mucous present in the oral cavity as well as blood, is ionically adhered to the teeth surfaces and cannot therefore be easily dislodged. The present invention combines the imaging probe to with an auxiliary which directs an air stream toward the surface to evaporate the film thereon even though the evaporative process is resisted by the surface tension of the film.

The rate at which liquid is evaporated by a stream of air flowing over its surface depends on the temperature of the air and its velocity. Hence, even when the temperature is fairly high, should the air stream then pass slowly over the liquid surface, the surface tension which acts as a skin covering the liquid will not be disrupted.

The external optical surfaces of the optical sensing probe have to be kept clean of any particles, film, etc., so as to retain good optical qualities required in order to be able to acquire a high quality image. The problem, however, is that the probe needs to be inserted into the oral cavity and consequently such optical surfaces may become coated, particularly by a liquid film, as a result of aerosol particles that exist in the oral cavity or liquid vapor that condenses on such surfaces. Thus, in accordance with one embodiment, the auxiliary provides also a gas stream that flows over such optical surfaces so as to clean such surfaces from any liquid film or droplets that may form thereon.

Figure 1:
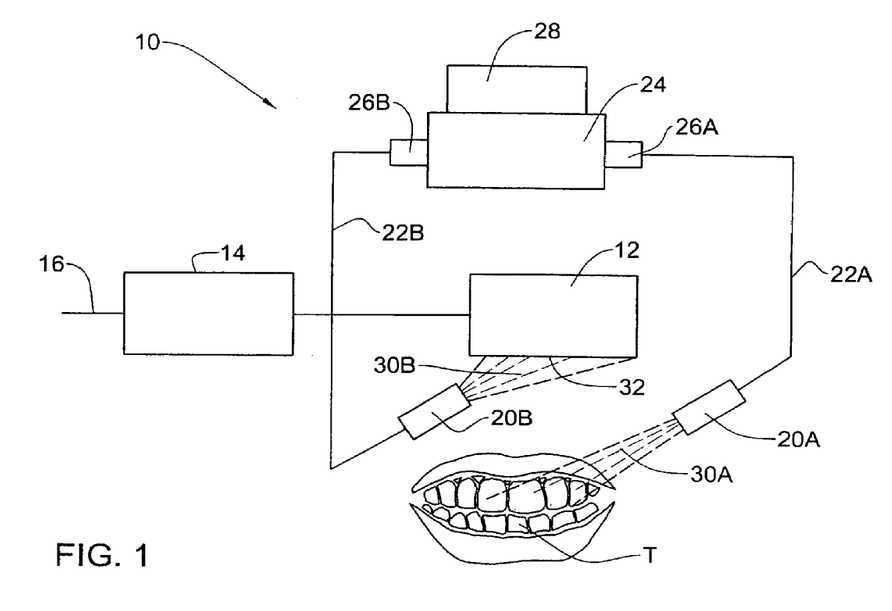
FIG. 1 shows a schematic illustration of an instrument with an auxiliary assembly in accordance with the invention.

Reference is first being made to FIG. 1, showing, in a schematic manner, an optical imaging instrument generally designated 10 that includes an optical probe 12 that can be inserted into the oral cavity and brought into proximity to teeth T and imaging optics and electronics assembly represented by block 14. Block 14 is coupled, through line 16 to an image analysis and data storage computer system (not shown).

The probe and the optical/electronic system may be that disclosed in PCT publication WO 00/00815, the content of which is incorporated herein by reference.

Probe 12 is associated with two nozzles 20A and 20B, each of which is linked through corresponding lines 22A and 22B to a source of pressurized gas 24. Source 24 may be a pressurized gas container or may be a compressor. The source of pressurized gas will typically be located outside the handheld probing instrument (not shown) that houses probe 12 and the optic/electronic assembly 14.

Each of lines 20A and 20B includes also a corresponding flow control valve 26A and 26B. It should be noted that rather than having independent lines, the two lines may combine through a manifold arrangement into a single line that leads to source 24.

In some embodiments of the invention, the gas is heated and a heating source 28 associated with the source of pressurized gas 24 may be provided. In other embodiments, rather than heating the gas at source, the gas may pass through a heat exchanger for online heating before reaching nozzles 20A and 20B. As will be appreciated, the gas is typically air although other gasses such as nitrogen, oxygen, and others.

Nozzle 20A is designed to eject a stream of gas 30A towards a segment of the teeth that is to be imaged. The rapid flow of gas, at times heated, over these surfaces, removes the liquid film which otherwise coats the surface of the teeth.

In one preferred embodiment of the invention, a second nozzle 20B is provided which directs the flow of gas 30B towards the optical surface 32 of probe 12. In this way a liquid film or droplets which would otherwise form on surface 32 are removed.

It should be noted that the instrument may at times be provided with more than one nozzle, such as nozzle 20A or nozzle 20B.

The above description was made in reference to an embodiment where a source of pressurized gas 24 causes a positive flow of gas towards the surface of the teeth T and the surface 32 of probe 12. In other embodiments of the invention, source 24 may be a suction pump giving rise to a negative-pressure air stream, namely from the surface towards the nozzles. A negative air stream will cause air in the oral cavity to flow over the teeth's surfaces, as well as over the optical surface 32 of probe 12 causing the removal of the liquid from such surfaces in this manner. One advantage of negative-pressure air stream is that it will also suck out the vapor evaporated from the liquid film.

Figure 2:
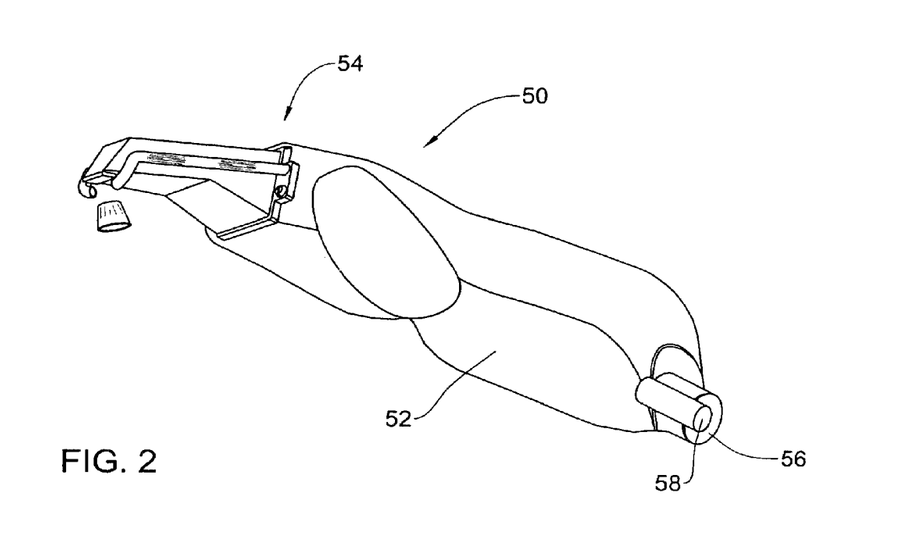
FIG. 2 is a perspective view of a dental imaging instrument incorporating an auxiliary assembly in accordance with the invention.
Figure 3:
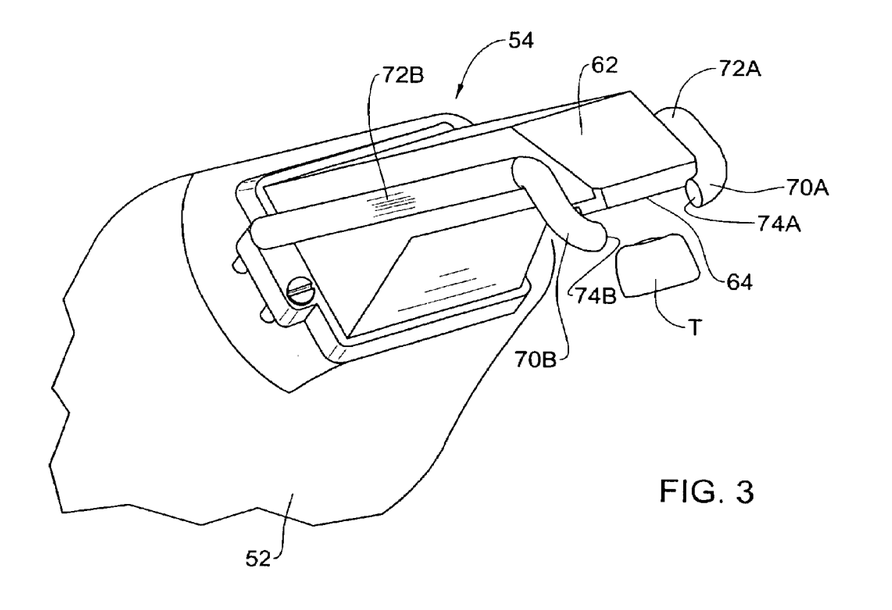
FIGS. 3 and 4 are close-up perspective views, from two different angles, of the front probing portion of the instrument of FIG. 2.
Figure 4:
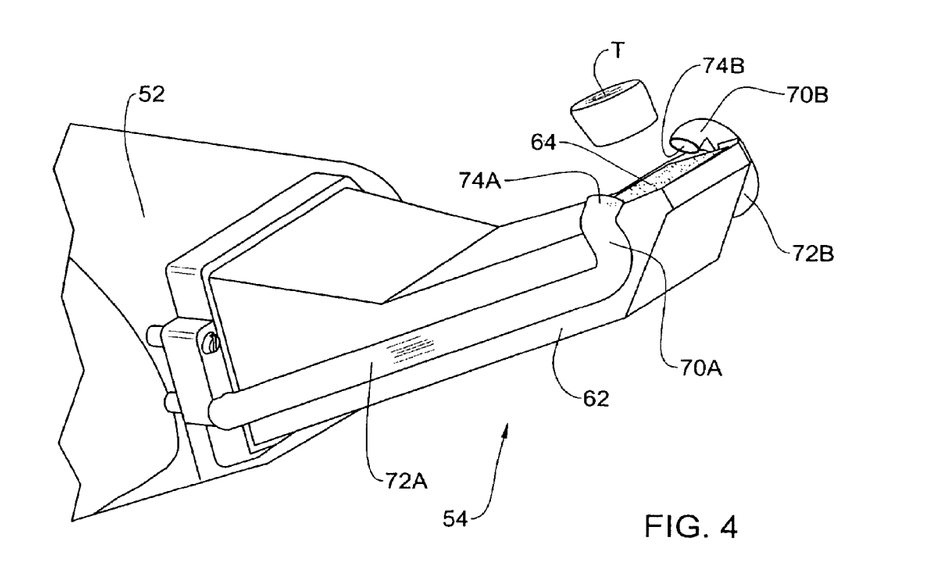

Reference is now being made to FIGS. 2, 3 and 4, showing a handheld probing instrument in accordance with an embodiment of the invention. Instrument 50 has a handle 52 and a head 54. Handle 52 houses the optics electronic assembly that is linked, through connector 56, to an image processing and image storage computers (not shown). Also shown at the rear of handle 52 is a conduit 58 for connecting to a source of pressurized gas (or a vacuum source in accordance with other embodiments of the invention).

The structure of head 54 is best seen in FIGS. 3 and 4. Head portion 54 includes an optical probe 62 designed in the manner shown in FIGS. 2A and 2B of the aforementioned PCT publication WO 00/00815. Optical probe 62 has an external probing glass surface 64 which in use is brought proximal to the teeth to be imaged. For the purpose of illustration, an image of a single tooth T in isolation being proximal and opposite probing glass surface 64, is shown.

Situated on two sides of probe 62 are nozzles 70A and 70B situated at the end of respective straight and rigid tubes 72A and 72B which are linked, through tubings within the handle/housing 52, to gas conduit 58. As can be seen, the opening 74A of nozzle 70A faces the surface to be imaged while opening 74B of nozzle 70B faces glass surface 64. By projecting air out of openings 74A and 74B of nozzles 70A and 70B surface 64 and surface of the tooth will be clean of liquid films or droplets.

In accordance with another embodiment, rather than ejecting gas out of these nozzles in a positive ejection fashion, a suction arrangement is provided for sucking air from such surfaces with a similar resulting effect.

What is claimed is:

1. A dental instrument for determining three dimensional (3D) topography of one or more teeth, said instrument comprising:
   a probe for scanning the one or more teeth so as to capture an image of surfaces of the one or more teeth in order to determine 3D topography of the surfaces of the one or more teeth by processing the image, said probe comprising a light source to generate an array of light beams, confocal optics to focus the array of light beams, a detector to detect light from the array of light beams that is reflected by the one or more teeth, so as to capture the image of the surfaces or the one or more teeth, and an external optical surface of the probe between the confocal optics and the one or more teeth; and
   an auxiliary coupled to the probe so as to direct a first stream of only gas over the teeth surfaces while also directing a second stream of only gas over the external optical surface of the probe, the auxiliary being coupled to the probe such that gas from the first stream is provided to the one or more teeth while scanning to clear material from the teeth surfaces and dry the teeth surfaces, so as to improve the image.

2. The instrument according to claim 1, wherein the first stream of only gas is emitted under positive pressure towards said teeth surfaces.

3. The instrument according to claim 2, wherein said gas is air.

4. The instrument according to claim 2, wherein the first stream of only gas is at a temperature above body temperature.

5. The instrument according to claim 2, wherein the auxiliary is coupled to an air compressor configured to produce positive pressure.

6. The instrument according to claim 1, wherein the first stream of only gas is under negative-pressure.

7. The instrument according to claim 6, wherein the auxiliary is coupled to a vacuum pump configured to produce negative pressure.

8. The instrument according to claim 1, wherein the auxiliary includes a pair of nozzles mounted on opposite sides of the probe.

9. The instrument according to claim 8, wherein the nozzles are oriented so that one nozzle produces the first stream of only gas on the surface of the one or more teeth to be imaged, and the other nozzle produces the second stream of only gas over the external optical surface of the probe.

10. A method for determining a three-dimensional (3D) surface topography of a tooth surface, the method comprising:
    bringing into proximity of the tooth surface a probe comprising a light source to generate an array of light beams, confocal optics to focus the array of light beams, and a detector to detect light from the array of light beams that is reflected by the tooth surface;
    acquiring an image of the tooth surface with the probe to determine 3D topography of the tooth surface by processing the image; and
    flowing a first stream of only gas over the tooth surface using an auxiliary coupled to the probe while flowing a second stream of only gas over an external optical surface of the probe, the auxiliary being coupled to the probe such that only gas from the first stream is provided to the tooth surface while acquiring the image to clear material from the tooth surface and dry the tooth surface, so as to improve the image.

11. The method according to claim 10, wherein the first stream of only gas is emitted under positive pressure towards the tooth surface.

12. The method according to claim 11, wherein said gas is air.

13. The method according to claim 10, wherein the first stream of only gas is under negative-pressure.

14. The method according to claim 10, wherein the first stream of only gas is at a temperature above body temperature.

15. The method according to claim 10, further comprising processing the image to produce digital data associated with the 3D topography of the tooth surface.

16. A dental instrument for determining the topography of one or more teeth, said instrument comprising:

a hand-held probe for scanning the one or more teeth so as to capture an image of surfaces of the one or more teeth in order to determine topography of the one or more teeth by processing the image, said probe comprising a light source to generate an array of light beams, confocal optics to focus the array of light beams, and a detector to detect light from the array of light beams that is reflected by the one or more teeth, so as to capture the image of the surfaces or the one or more teeth; and an auxiliary coupled to the hand-held probe so as to direct a first stream of only gas over the teeth surfaces while a second stream of only gas is directed to an external optical sensing surface, the auxiliary being coupled to the probe such that only gas is provided to the one or more teeth while scanning to clear material from the teeth surfaces and dry the teeth surfaces, so as to improve the image.

* * * * *